US006960705B2

(12) United States Patent
Wei et al.

(10) Patent No.: US 6,960,705 B2
(45) Date of Patent: Nov. 1, 2005

(54) **NUCLEIC ACID ENCODING A HYPERSENSITIVE RESPONSE ELICITOR FROM *XANTHOMONAS CAMPESTRIS***

(75) Inventors: Zhong-Min Wei, Kirkland, WA (US); Shane S. Swanson, Seattle, WA (US); Hao Fan, Bothell, WA (US)

(73) Assignee: Eden Bioscience Corporation, Bothell, WA (US)

( * ) Notice: Subject to any disclaimer, the term of this patent is extended or adjusted under 35 U.S.C. 154(b) by 379 days.

(21) Appl. No.: 09/829,124

(22) Filed: Apr. 9, 2001

(65) Prior Publication Data

US 2002/0066122 A1 May 30, 2002

Related U.S. Application Data

(63) Continuation-in-part of application No. 09/412,452, filed on Oct. 4, 1999, now abandoned.
(60) Provisional application No. 60/224,053, filed on Aug. 9, 2000, and provisional application No. 60/103,124, filed on Oct. 1, 1998.

(51) Int. Cl.[7] .............................. A01H 5/00; A01H 5/10; C12N 15/82; C12N 15/31
(52) U.S. Cl. ...................... 800/301; 800/279; 800/290; 536/23.7; 435/419; 435/252.3; 435/320.1
(58) Field of Search ................................. 800/279, 290, 800/301, 288, 298, 305, 317.1, 306, 317.2, 307, 317.3, 309, 317.4, 310, 320.1, 311, 320.2, 312, 320.3, 313, 314, 315, 316, 317, 318, 320, 322, 323, 321, 323.2, 323.3; 536/23.7; 435/419, 252.2, 320.1, 468, 418, 411, 412, 414, 415, 417, 416

(56) References Cited

U.S. PATENT DOCUMENTS

| | | |
|---|---|---|
| 4,569,841 A | 2/1986 | Liu |
| 4,597,972 A | 7/1986 | Taylor |
| 4,601,842 A | 7/1986 | Caple et al. |
| 4,740,593 A | 4/1988 | Gonzalez et al. |
| 4,851,223 A | 7/1989 | Sampson |
| 4,886,825 A | 12/1989 | Ruess et al. |
| 4,931,581 A | 6/1990 | Schurter et al. |
| 5,057,422 A | 10/1991 | Bol et al. |
| 5,061,490 A | 10/1991 | Paau et al. |
| 5,135,910 A | 8/1992 | Blackburn et al. |
| 5,173,403 A | 12/1992 | Tang |
| 5,217,950 A | 6/1993 | Blackburn et al. |
| 5,243,038 A | 9/1993 | Ferrari et al. |
| 5,244,658 A | 9/1993 | Parke |
| 5,260,271 A | 11/1993 | Blackburn et al. |
| 5,348,743 A | 9/1994 | Ryals et al. |
| 5,494,684 A | 2/1996 | Cohen |
| 5,523,311 A | 6/1996 | Schurter et al. |
| 5,550,228 A | 8/1996 | Godiard et al. |
| 5,552,527 A | 9/1996 | Godiard et al. |
| 5,708,139 A | 1/1998 | Collmer et al. |
| 5,850,015 A | 12/1998 | Bauer et al. |
| 6,001,959 A | 12/1999 | Bauer et al. |
| 6,277,814 B1 * | 8/2001 | Qiu et al. .................... 514/2 |

FOREIGN PATENT DOCUMENTS

| | | |
|---|---|---|
| EP | 0 612 848 A3 | 2/1994 |
| WO | WO 93/23532 | 11/1993 |
| WO | WO 94/01546 | 1/1994 |
| WO | WO 94/26782 | 11/1994 |
| WO | WO 95/19443 | 7/1995 |
| WO | WO 96/39802 | 12/1996 |
| WO | WO 98/15547 | 4/1998 |
| WO | WO 98/24297 | 6/1998 |
| WO | WO 98/32844 | 7/1998 |
| WO | WO 98/37752 | 9/1998 |
| WO | WO 98/54214 | 12/1998 |
| WO | WO 99/07206 | 2/1999 |
| WO | WO 99/07207 | 2/1999 |
| WO | WO 00/28055 | * 5/2000 |
| WO | WO 01/98501 | * 12/2001 |
| WO | WO 02/37960 | * 5/2002 |

OTHER PUBLICATIONS

US 5,650,387, 7/1997, Wei et al. (withdrawn)
Gopalan et al, 1996, Plant Dis. 80:604–610.*
Bauer et al, 1995, MPMI 8:484–91.*
Cui et al, 1996, MPMI 9:565–573.*
Ahmad et al, 1996, 8th Int'l Cong. Molec. Plant Microbe Inter.*
Preston et al, 1995, MPMI 8:717–732.*
Bonas, 1994, Current Tpoics in Microbiol. Immunol. 192:79–98.*
Alfano et al, 1997, J. Bacteriol. 179:5655–5662.*
Swanson et al, 1999, Phytopath. 90:S75.*
Bogdanove et al, 1996, Molec. Microbiol. 20:681–683.*
Wei et al, 2000, MPMI 13:1251–1262.*
Strobel et al, 1996, Plant J. 9:431–439.*
Bonas 1994, Trends Microbiol 2:1–2.*
Wei et al, 1996, Acta Hort. 411:223–225.*
Koncz et al, 1983, EMBO J. 2:597–1603.*
Lund et al, 1992, Plant Mol. Biol. 18:47–53.*
Ausubel et al, 1998, Current Protocols in Molecular Biology, vol. 1, p. 6.3.5–6 and 6.4.3–9.*

(Continued)

*Primary Examiner*—Anne Kubelik
(74) *Attorney, Agent, or Firm*—Nixon Peabody LLP

(57) ABSTRACT

The present invention is directed to an isolated DNA molecule encoding a *Xanthomonas campestris* hypersensitive response elicitor protein or polypeptide. The DNA molecule that encodes such protein has the following uses: imparting disease resistance to plants, enhancing plant growth, controlling insects on plants, imparting stress resistance, imparting post-harvest disease resistance, maximizing the benefit of or overcoming a yield penalty associated with a transgenic trait, inhibiting desiccation of cuttings from ornamental plants, and promoting early flowering of an ornamental plant. These can be achieved by expression of the hypersensitive response elicitor in transgenic plants. Transgenic plants, plants seeds, and cuttings from such transgenic plants are also disclosed.

21 Claims, 1 Drawing Sheet

OTHER PUBLICATIONS

Figure 1:
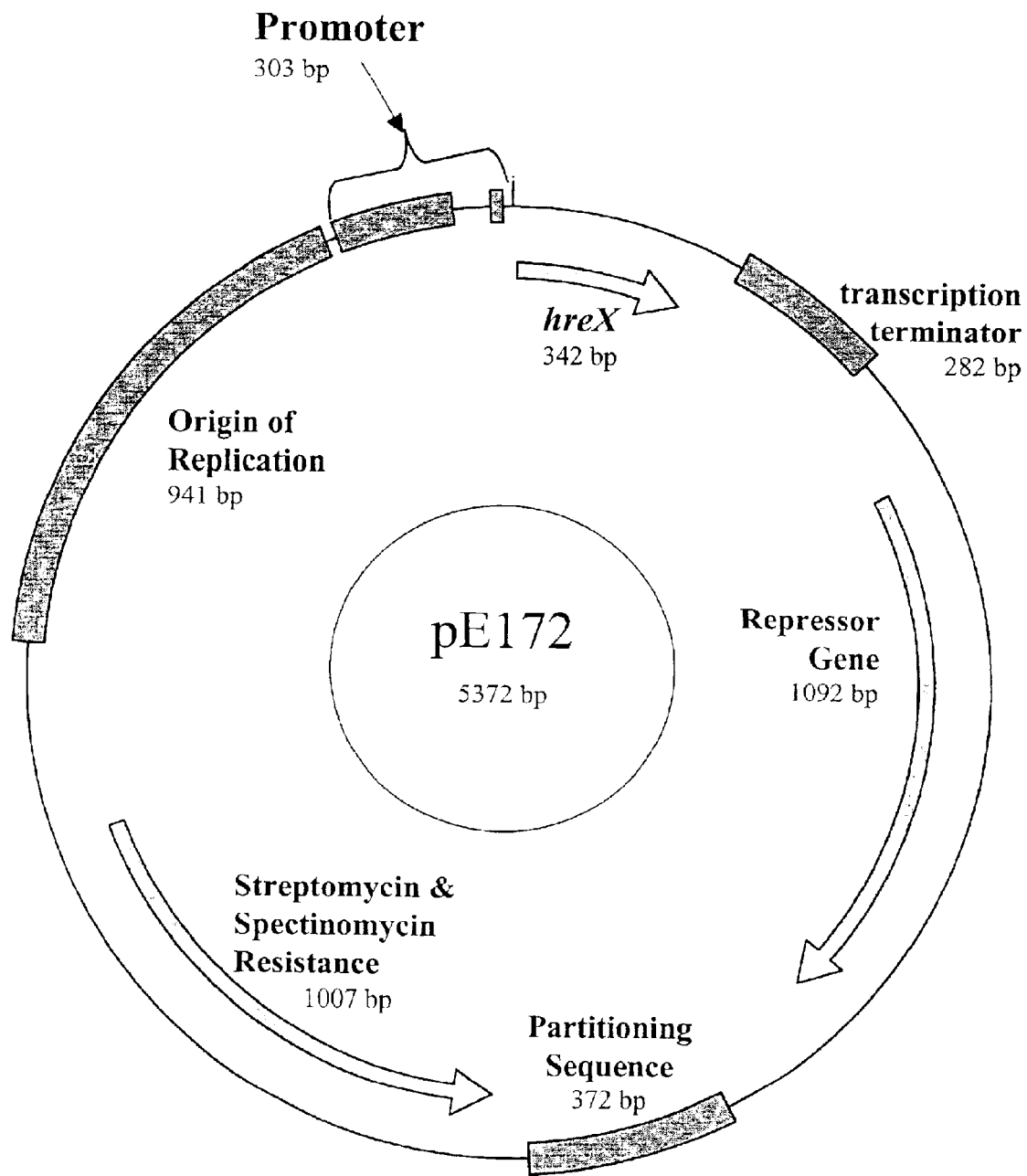

Rugang et al, 1999, Science in China 42:96–101.*
Keller et al. Pathongen–Induced Elicitin Production in Transgenic Tobacco Generates a Hypersensitive Response and Nonspecific Disease Resistance. Feb. 1999 The Plant Cell, vol. 11, 223–235.*
Hill et al. Functional Analysis of Conserved Histidines in ADP_Glucose Pyrophosphorylase from *Escherichia coli*, 1998. Biochemical and Biophysical Reserch Communications 244, 573–577.*
Lazar et al. Transforming Growth Factor : Mutation of Asartic Acid 47 and Leucine 48 Results in Different Biological Activities. Mar. 1988. Molecular and Cellula Biology, p. 1247–1252.*
Frederick et al., "The WTS Water–Soaking Genes of *Erwinia stewartii* are Related to hrp Genes," Seventh International Symposium on Molecular Plant Microbe Ineractions, Abstract No. 191 (Jun. 1994).
Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).
Preston et al., "The HrpZ Proteins of *Pseudomonas syringae* pvs. *syringae, glycinea*, and *tomato* are Encoded by an Operon Containing *Yersinia ysc* Homologs and Elicit the Hypersensitive Response in Tomato but not Soybean," *Mol. Plant–Microbe Interact.*, 8(5):717–32 (1995).
Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).
Stryer, L., "Enzymes are Highly Specific," *Biochemistry*, San Francisco: W.H. Freeman and Company, p. 116 (1975).
Keen et al., "Inhibition of the Hypersensitive Reaction of Soybean Leaves to Incompatible Pseudomonas spp. by Blasticidin S, Streptomycin or Elevated Temperature," *Physiological Plant Pathology*, 18:325–337 (1981).
Lerner, R.A., "Tapping the Immunological Repertoire to Produce Antibodies of Predetermined Specificity," *Nature*, 299:592–96 (1982).
Staskawicz et al., "Cloned Avirulence Gene of *Pseudomonas syringae* pv. *glycinea* Determines Race–specific Incompatibility on *Glycine max* (L.) Merr.," *Proc. Natl. Acad. Sci. USA*, 81:6024–28 (1984).
Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).
Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).
Huang et al., "The *Pseudomonas syrnigae* pv. *syringae* 61 htpH Product, an Envelope Protein Required for Elicitation of the Hypersensitive Response in Plants," *J. Bacteriol.*, 174(21):6878–85 (1992).
Bonas, U., "hrp Genes of Phytopathogenic Bacteria," *Current Topics in Microbio.*, 192:79–98 (1994).
Arlat et al., "PopA1, A Protein Which Induces a Hypersensitivity–Like Response on Specific Protein Petunia Genotypes, is Secreted via the Hrp Pathway of *Pseudomonas solanacearum*", *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).
Kelman, A., "The Relationship of Pathogenicity in *Pseudomonas solanacearum* To Colony Appearance on a Tetrazolium Medium," *Phytopathology*, 44:693–95 (1954).
Winstead et al., "Inoculation Techniques For Evaluating Resistance to *Pseudomonas solanacearum*," *Phytopatholog*, 42:628–34 (1952).
Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).
Anderson et al., "Responses of Bean to Root Colonization with *Pseudomonas putida* in a Hydroponic System," *Phytopathology*, 75(9):992–95 (1985).
Gardner et al., "Growth Promotion and Inhibition by Antibiotic–Producing Fluorescent Pseudomonads on Citrus Roots," *Plant and Soil*, 77:103–13 (1984).
Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).
Atkinson et al., "The Hypersensitive Reaction of Tobacco to *Pseudomonas syringae* pv. *pisi*," *Plant Physiol.*, 79:843–47 (1985).
Huynh et al., "Bacterial Blight of Soybean: Regulation of a Pathogen Gene Determining Host Cultivar Specificity," *Science*, 245:1374–77 (1986).
Kloepper et al., "Plant Growth–Promoting Rhizobacteria on Canola (Rapeseed)," *Plant Disease*, 72(1):42–6 (1988).
Kloepper et al., "Enhanced Plant Growth by Siderophores Produced by Plant Growth–Promoting Rhizobacteria," *Nature*, 286:885–86 (1980).
Kloepper et al., "Pseudomonas Siderophores: A Mechanism Explaining Disease–Suppressive Soils," *Current Microbiology*, 4:317–20 (1980).
Kloepper et al., "Emergence–Promoting Rhizobacteria: Description and Implications for Agriculture," In: *Iron, Siderophores, and Plant Disease*, Swinbome (ed), Plenum, NY, 155–64 (1986).
Kloepper et al., "Relationship of in vitro Antibiosis of Plant Growth–Promoting Rhizobacteria to Plant Growth and the Displacement of Root Microflora," *Phytopathology*, 71(10):1020–24 (1981).
Kloepper et al., "Effects of Rhizosphere Colonization by Plant Growth–Promoting Rhizobacteria on Potato Plant Development and Yield", *Phytopathology*, 70(11):1078–82 (1980).
Kloepper et al., "Plant Growth Promotion Mediated by Rhizosphere Bacterial Colonizers," In: *The Rhizosphere and Plant Growth*,—315–32, Keister et al. (eds), pp. 315–326 (1991).
Liftshitz et al., "Growth Promotion of Canola (rapeseed) Seedlings by a Strain of *Psuedomonas putida* Under Gnotobiotic Conditions," Conditions, *Microbiol*, 33:390–95 (1987).
Liu et al., "Induction of Systemic Resistance in Cucumber Against Bacterial Angular Leaf Spot by Plant Growth–Promoting Rhizobacteria," *Phytopathology*, 85(8):843–47 (1995).
Loper et al., "Influence of Bacterial Sources of Indole–3–acetic Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512–22 (1986).

Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425–429 (1987).

Wei et al., "Induction of Systemic Resistance of Cucumber to *Colletotrichum orbiculare* by Select Strains of Plant Growth–Promoting Rhizobacteria," *Phytopathology*, 81:1508–12 (1991).

Weller, D.M., "Biological Control of Soilborne Plant Pathogens in the Rhizosphere with Bacteria," *Ann. Rev. Phytopathol.*, 26:379–407 (1988).

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection" *Science*, 250:1002–04 (1990).

Cameron et al., "Biologically Induced Systemic Acquired Resistance in *Arabidopsis thaliana*," *The Plant Journal*, 5(5):715–25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Micorbiol.*, 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli*," *Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Bonnet, et al., "Induction de nécroses foliaires, de protéines b et de résistance dans les interactions tabac Phytophthora," *Agronomie*, 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).

Kang et al., "Control of Tomato Disease by Interference of an Attenuated Virus," *Res. Rept. RDA (Hort)*, 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya, Biologiya* 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).

Shields, R., "Towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748–56 (1988).

Ricci, et al., "Differential Production of Parasiticein, an Elicitor of Necrosis and Resistance in Tobacco, by Isolates of *Phytophthora parasitica*," *Plant Pathology*, 41:298–307 (1992).

Honée, et al., "Molecular Characterization of the Interaction Between the Fungal Pathogen *Cladosporium fulvum* and tomato," *Advances in Molecular Genetics of Plant–Microbe Interactions*, 3:199–206 (1994).

Keller, et al., "Responses of Tobacco to Elicitins, Proteins From *Phytophthora spp.* Eliciting Acquired Resistance," *Advances in Molecular Genetics of Plant–Microbe Interactions*, 3:327–32 (1994).

Keen, et al., "Bacterial Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi hrp* Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum*, (syn. *Fulvia fulva*)," *Physiological and Molecular Plant Pathology*, 33:59–67 (1988).

Steinberger et al., "Creation and Complementation of Pathogenicity Mutants of *Erwinia amylovora*," *Molecular Plant–Microbe Interactions*, 1(3):135–44 (1988).

Beer et al., "The Hypersensitive Response is Elicited by *Escherichia coli* Containing a Cluster of Pathogenicity Genes From *Erwinia amylovora*," *Phytopathology*, 79(10):1156 (Abstract 169) (1989).

Hiatt et al., "Production of Antibodies in Transgenic Plants," *Nature*, 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).

Huang et al., "Isolation and Purification of a Factor from *Pseudomonas solanacearum* That Induces a Hypersensitive–like Response in Potato Cells," *Molecular Plant–Microbe Interactions*, 2(3):132–38 (1989).

James et al., "Genetic Transformation of Apple (*Malus pumila* Mill.) Using a Disarmed Ti–binary Vector," *Plant Cell Reports*, 7:658–61 (1989).

Laby et al., "Cloning and Preliminary Characterization of an hrp Gene Cluster of *Erwinia amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–98 (1990).

Walters et al., "Gene for Pathogenicity and Ability to Cause the Hypersensitive Reaction Cloned from *Erwinia amylovora*," *Physiological and Molecular Plant Pathology*, 36:509–21 (1990).

Wu et al., "Cloning, Genetic Organization, and Characterization of a Structural Gene Encoding Bacillopeptidase F from *Bacillus subtilis*," *The Journal of Biological Chemistry*, 265(12):6845–50 (1990).

Bauer et al., "Futher Characterization of an hrp Gene Cluster of *Erwinia amylovora*," *Molecular Plant–Microbe Interactions*, 4(5):493–99 (1991).

Beer et al., "The htp Gene Cluster of *Erwinia amylovora*," *Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–74 (1991).

Milat et al., "Physiological and Structural Changes in Tobacco Leaves Treated with Cryptogein, a Proteinaceous Elicitor From *Phytophthora cryptogea*," *Phytopathology*, 81(11):1364–68 (1991).

Ruberti et al., "A Novel Class of Plant Proteins Containing a Homeodomain with a Closely Linked Leucine Zipper Motif," *The EMBO Journal*, 10(7):1787–91 (1991).

Quigley et al., "Nucleotide Sequence and Expression of a Novel Glycine–Rich Protein Gene from *Arabidopsis thaliana*," *Plant Molecular Biology*, 17:949–52 (1991).

Van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–9 (1991).

Waldmann, T.A., "Monoclonal Antibodies in Diagnosis and Therapy," *Science*, 252:1657–62 (1991).

Willis et al., "hrp Genes of Phytopathogenic Bacteria," *Molecular Plant–Microbe Interactions*, 4:(2) 132–38 (1991).

Beer et al., "Are Harpins Universal Elicitors of the Hypersensitive Response of Phytopathogenic Bacteria?," *Advances in Molecular Genetics of Plant–Microbe Interactions*, 2:281–86 (1992).

Laby et al., "Hybridization and Functional Complementation of the hrp Gene Cluster from *Erwinia amylovora* Strain Ea321 With DNA of Other Bacteria," *Molecular Plant–Microbe Interactions*, 5(5):412–19 (1992).

Sandhu, "Protein Engineering of Antibodies," *Crit. Rev. in Biotech.*, 12(5/6):437–62 (1992).

Wei et al., "Harpin, Elicitor of the Hypersensitive Response Produced by the Plant Pathogen *Erwinia amylovora*," *Science*, 257:85–8 (1992).

He et al., "*Pseudomonas syringae* pv. *syringae* Harpin$_{Pss}$: A Protein that is Secreted via the Hrp Pathway and Elicits the Hypersensitive Response in Plants," *Cell*, 73:1255–66 (1993).

Bonas, U., "Bacterial Home Goal by Harpins," *Trends in Microbiology*, 2:1–2 (1994).

Boccara, et al., "Plant Defense Elicitor Protein Produced by *Erwinia chrysanthemi*," *Mechanisms of Plant Defense Responses*, p. 166 (1993).

Qui et al., "Treatment of Tomato Seed with Harpin Enhances Germination and Growth and Induces Resistance to *Ralstonia solanacearum*," *Phytopathology*, 87:6, S80 (1997) (abstract only).

Burr et al., "Increased Potato Yields by Treatment of Seedpieces with Specific Strains of *Pseudomonas fluorescens* And *P. putida*," *Phytopathology*, 68:1377–1383 (1978).

Ricci et al., "Proteinaceous Elicitors of Plant Defense Responses," B. Fritig eds., *Mechanisms of Plant Defense Responses*, Netherlands, pp. 121–130 (1993).

Keen et al., "Syringolide Elicitors Specified By Avirulence Gene D Alleles In *Pseudomonas syringae*," *Advances in Molecular Genetics of Plant–Microbe Interactions*, 3:41–48 (1994).

Klessig et al., "The Salicylic Acid Signal In Plants," *Plant Molecular Biology*, 26:1439–1458 (1994).

Bogdanove et al., "Unified Nomenclature For Broadly Conserved hrp Genes of Phytopathogenic Bacteria," *Molecular Microbiology*, 20(3):681–683 (1996).

Bonnet et al., "Acquired Resistance Triggered By Elicitins In Tobacco and Other Plants," *European Journal of Plant Pathology*, 102:181–192 (1996).

Cui et al., "The RsmA⁻Mutants of *Erwinia carotovora* subsp. *carotovora* Strain Ecc71 Overexpress hrpN$_{Ecc}$ and Elicit a Hypersensitive Reaction–like Response in Tobacco Leaves," *Molecular Plant–Microbe Interactions*, 9(7):565–573 (1996).

Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell*, 8:1809–1819 (1996).

Wei et al., "Induced Systemic Resistance to Cucumber Dieseases and Increased Plant Growth by Plant Growth–Promoting Rhizobacteria Under Field Conditions," *Phytopathology*, 86:221–224 (1996).

Wengelnik et al., "Expression and Localization of HrpA1, a Protein of *Xanthomonas campestris* pv. vesicatoria Essential for Pathogenicity and Induction of the Hypersensitive Reaction," *Journal of Bacteriology*, 178:1061–1069 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance To *Xanthomonas campetris* pv. *oryzae* In Rice," *Physiological and Molecular Plant Pathology*, 51:243–257 (1997).

Alfano et al., "Analysis of the Role of the Pseudomonas Syringae pv. Syringae HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19:715–728 (1996).

Linthorst et al., "Constitutive Expression of Pathogenesis–Related Proteins PR–1, GRP, and PR–S in Tobacco Has No Effect on Virus Infection," *The Plant Cell*, 1:285–291 (1989).

Malamy et al., Salicylic Acid and Plant Disease Resistance, *The Plant Journal*, 2:643–654 (1992).

McGurl et al., "Structure, Expression, and Antisense Inhibition of the Systemin Precursor Gene," *Science*, 255:1570–1573 (1992).

Wei et al., "hrpL Activates *Erwinia amylovora* hrp Gene Transcription and Is a Member of the ECF Subfamily of σ Factors," *Journal of Bacteriology*, 177:6201–6210 (1995).

Nissinen et al., "Clavibacter Michiganensis Subsp. Sepedonicus Elicits a Hypersensitive Response in Tobacco and Secretes Hypersensitive Response–Inducing Protein," *Phytopathology*, 87:678–684 (1997) (Abstract only).

Schulte et al., Expression of the *Xanthomonas campestris* pv. Vesicatoria hrp Gene Cluster, Which Determines Pathogenicity and Hypersensitivity on Pepper and Tomato, Is Plant Inducible, *Journal of Bacteriology*, 174:815–823 (1992).

Yu, "Elicitins from Phytophthora and Basic Resistance in Tobacco," *Proc. Natl. Acad. Sci. USA*, 92:4088–4094 (1995).

Wu et al., "Disease Resistance Conferred by Expression of a Gene Encoding $H_2O_2$–Generating Glucose Oxidase in Transgenic Potato Plants," *The Plant Cell*, 7:1357–1368 (1995).

Kim et al., "HrpW of *Erwinia amylovora*, a New Harpin That Contains a Domain Homologous to Pectate Lyases of a Distinct Class," *Journal of Bacteriology* 180:5203–5210 (1998).

Charkowski et al., "The *Pseudomonas syringae* pv. Tomato HrpW Protein Has Domains Similar to Harpins and Pectate Lyases and Can Elicit the Plant Hypersensitive Response and Bind to Pectate," *Journal of Bacteriology* 180:5211–5217 (1998).

Lorang et al., "Characterization of avrE from *Pseudomonas syringae* pv. Tomato: A hrp–Linked Avirulence Locus Consisting Of at Least Two Transcriptional Units," *MPMI* 8:49–57 (1995).

Wei et al., "HrpI of *Erwinia amylovora* Functions in Secretion of Harpin and Is a Member of a New Protein Family," *J. Bacteriology* 175(24):7958–7967 (1993).

Swanson et al., "Isolation and Characterization of an HR Elicitor from *Xanthomonas campestris*," *Phytopathology* 88(9):S87 (1998).

Swanson et al., "Isolation of the hreX Gene Encoding the HR Elicitor Harpin (Xcp) from *Xanthamonas campestris* pv. *pelargonii*", *Phytopathology* 90:S75 (abstract) 1998.

Collmer et al., "*Erwinia chyrsanthemi* and *Pseudomonas syringae*: Plant Pathogens Trafficking in Extracellular Virulence Proteins," *Current Topics in Microbiology and Immunology*, 192:43–78 (1994).

Wei et al., "Induction of Systemic Resistance with Seed Treatment by PGPR Strains," *Bulletin of the International Organization for Biological and Integrated Control of Noxious Animals and Plants, Western Paleartic Regional Section*, pp. 191–194 (1991).

Young et al., "PGPR: Is There a Relationship Between Plant Growth Regulators and the Stimulation of Plant Growth or Biological Activity?," In: Keel et al., eds., *The Second International Workshop on Plant Growth–Promoting Rhizobacteria, IOBC/WPRS Bulletin*, Interlaken, Switzerland, pp. 182–186 (Oct. 14–19, 1990).

Dean et al., "Immunisation Against Disease: The Plant Fights Back," *British Mycological Society Symposium*, pp. 383–410 (1988).

Rugang et al., "Reduction of Lesion Growth Rate of Late Blight Plant Disease in Transgenic Potato Expressing Harpin Protein," *Science in China (Series C)* 42(1):96–101 (1999).

da Silva et al., "Comparison of the Genomes of Two Xanthomonas Pathogens with Differing Host Specificities," *Nature* 417:459–463 (2002).

Noël et al., "Two Novel Type III–Secreted Proteins of *Xanthomonas campestris* pv. vesicatoria Are Encoded within the hrp Pathogenicity Island," *J. of Bacteriology* 184(5):1340–1348 (2002).

Zhu et al., "Identification of Two Novel hrp–Associated Genes in the hrp Gene Cluster of *Xanthomonas oryzae* pv. oryzae," *J. of Bacteriology* 182(7):1844–1853 (2000).

* cited by examiner

NUCLEIC ACID ENCODING A HYPERSENSITIVE RESPONSE ELICITOR FROM *XANTHOMONAS CAMPESTRIS*

This application claims benefit of U.S. Provisional Patent Application Ser. No. 60/224,053 filed Aug. 9, 2000; this application is also a continuation-in-part of U.S. patent application Ser. No. 09/412,452 now abandoned filed Oct. 4, 1999, which claims the benefit of U.S. Provisional Patent Application Ser. No. 60/103,124 filed Oct. 1, 1998.

FIELD OF THE INVENTION

The present invention relates to a hypersensitive response elicitor from *Xanthomonas campestris,* its encoding DNA, and their uses.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring without progressive disease symptoms. During compatible interactions on host plants, bacterial populations increase dramatically and progressive symptoms occur. During incompatible interactions, bacterial populations do not increase, and progressive symptoms do not occur.

The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise,* Vol. 5, J. G. Horsfall and E. B. Cowling, ed. Academic Press New York (1980); Klement, Z., "Hypersensitivity," pages 149–177 in: *Phytopathogenic Prokarvotes,* Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199:299–300; Klement, et al., "Hypersensitive Reaction Induced by Phytopathogenic Bacteria in the Tobacco Leaf," *Phytopatholoy* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes,* Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes,* Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in Gram-negative plant pathogens, where they are clustered, conserved, and in some cases interchangeable (Willis, D. K., et al., "hrp Genes of Phytopathogenic Bacteria," *Mol. Plant-Microbe Interact.* 4:132-138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms,* J. L. Dangl, ed. Springer-Verlag, Berlin (1994)). Several hrp genes encode components of a protein secretion pathway similar to one used by *Yersinia, Shigella,* and *Salmonella* spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae,* and *P. solanacearum,* hrp genes have been shown to control the production and secretion of glycine-rich protein elicitors of the hypersensitive response (He, S. Y., et al. "*Pseudomonas Syringae* pv. *Syringae* HarpinPss: a Protein that is Secreted via the Hip Pathway and Elicits the Hypersensitive Response in Plants," *Cell* 73:1255–1266 (1993), Wei, Z. -M., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-Like Response on Specific *Petunia* Genotypes, is Secreted via the Hrp Pathway of *Pseudomonas solanacearum,*" *EMBO J.* 13:543–553 (1994)).

The first of these proteins was discovered in *E. amylovora,* a bacterium that causes fire blight of rosaceous plants, and was designated harpin (Wei, Z. -M., et al, "Harpin, Elicitor of the Hypersensitive Response Produced by the Plant Pathogen *Erwinia amylovora,*" *Science* 257:85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI10000 PopA1 protein has similar physical properties and also elicits the hypersensitive response in leaves of tobacco, which is not a host of that strain (Arlat, et al. "PopA1, a Protein Which Induces a Hypersensitive-like Response on Specific *Petunia* Genotypes, is Secreted via the Hip Pathway of *Pseudomonas solanacearum,*" *EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among Gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* $\text{Harpin}_{Ech}$: Soft-Rot Pathogenesis," *MPMI* 8(4): 484–91 (1995)); *Erwinia carotovora* (Cui, et. al., "The $\text{RsmA}^-$ Mutants of *Erwinia carotovora* subsp. *carotovora* Strain Ecc71 Overexpress $\text{hrpN}_{Ecc}$ and Elicit a Hypersensitive Reaction-like Response in Tobacco Leaves," *MPMI* 9(7): 565–73 (1996)); *Erwinia stewartii* (Ahmad, et. al., "Harpin is not Necessary for the Pathogenicity of *Erwinia stewartii* on Maize," *8th Int'l. Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg. Am. Phytopath. Soc.* Jul. 27–31, 1996); and *Pseudomonas syringae* pv. *syringae* (WO 94/26782 to Cornell Research Foundation, Inc.).

The present invention is a further advance in the effort to identify, clone, and sequence hypersensitive response elicitor proteins or polypeptides from plant pathogens.

SUMMARY OF THE INVENTION

The present invention is directed to an isolated hypersensitive response eliciting protein or polypeptide from *Xanthomonas campestris* as well as a DNA molecule encoding that protein or polypeptide.

The hypersensitive response eliciting protein or polypeptide can be used to impart disease resistance to plants, enhance plant growth, control insects, impart stress resistance to plants, impart post-harvest disease or desiccation resistance in fruits or vegetables, impart desiccation resistance to cuttings of ornamental plants, and promote early flowering of ornamental plants. These various uses involve applying the hypersensitive response elicitor protein or polypeptide in a non-infectious form to plants or plant seeds under conditions effective to impart disease resistance, enhance plant growth, control insects, impart stress resistance on plants or plants grown from the plant seeds; applying the hypersensitive response elicitor protein or polypeptide in a non-infectious form to plants or fruits or vegetables under conditions effective to impart post-harvest disease or desiccation resistance; applying the hypersensitive response elicitor in non-infectious form to ornamental plants under conditions effective to promote early flowering of the ornamental plants or inhibit desiccation of cuttings removed from the ornamental plants; or applying the hypersensitive response elicitor in non-infectious form to cuttings removed from ornamental plants for purposes of inhibiting desiccation of the cuttings.

As an alternative to topically applying the hypersensitive response elicitor protein or polypeptide to plants, plant seeds, cuttings, fruits, or vegetables, transgenic plants or plant seeds can be utilized. When utilizing transgenic plants, this involves providing a transgenic plant transformed with a DNA molecule encoding the hypersensitive response elicitor protein or polypeptide of the present invention and growing the plant under conditions effective to impart disease resistance, enhance plant growth, control insects, and/or impart stress resistance in the plants or plants grown from the plant seeds; to impart post-harvest disease or desiccation resistance to fruits or vegetables; to promote early flowering of transgenic ornamental plants; or to inhibit desiccation of cuttings removed from transgenic ornamental plants. Alternatively, a transgenic plant seed transformed with the DNA molecule encoding a hypersensitive response elicitor protein or polypeptide can be provided and planted in soil. A plant is then propagated under conditions effective to impart disease resistance, enhance plant growth, control insects on plants or plants grown from the plant seeds; impart post-harvest disease or desiccation resistance to fruits or vegetables harvested from the transgenic plants; promote early flowering of ornamental plants; and impart desiccation resistance to cuttings removed from ornamental.

By either (i) simultaneously introducing a value-added trait and a trait for expression of the hypersensitive response elicitor of the present invention into a plant line or (ii) topically applying the hypersensitive response elicitor of the present invention to a transgenic plant line expressing a value-added trait, it is possible to obtain a transgenic plant line from which the maximal benefit of the value-added trait can be realized. For example, value-added traits which offer strong but limited benefits (e.g., resistance to a particular pathogen) can be fully realized either by transforming the plants with a transgene or DNA molecule encoding the hypersensitive response elicitor of the present invention or applying the hypersensitive response elicitor of the present invention to the plants, both of which will further enhance the same trait by imparting broad growth enhancement, stress tolerance, disease resistance, and/or insect resistance. Similarly, value-added traits which result in a concomitant yield penalty can be fully realized either by transforming the plants with a transgene or DNA molecule encoding the hypersensitive response elicitor of the present invention or applying the hypersensitive response elicitor of the present invention to the plants, both of which will overcome the yield penalty by imparting broad growth enhancement, stress tolerance, disease resistance, and/or insect resistance. When expression is utilized rather than topical application, a transgenic germplasm that expresses the hypersensitive response elicitor of the present invention (i.e., already has enhanced disease resistance and yield properties beyond what is available from conventional hybrid lines) can be transformed with a transgene conferring a specific value-added trait. The same can be said for subsequent introduction of a transgene coding for hypersensitive response elicitor expression into a transgenic germplasm that already expresses a specific value-added trait. Any of these approaches will likely minimize or eliminate any disadvantages relative to conventional hybrids.

BRIEF DESCRIPTION OF THE DRAWING

FIG. 1 illustrates the components of expression vector pE172, which includes the hreX coding sequence under control of a lacO promoter sequence and transcription terminator, both from *E. coli.* The pE172 vector also includes a lacI repressor gene from *E. coli,* a partition region (par) from pGB2 (Churchward et al., *Gene* 31:165–171 (1984), which is hereby incorporated by reference in its entirety), a streptomycin/spectinomycin resistance gene (aadA) from pGB2, and a narrow host range origin of replication (oriV) from pMB1 for replication in Enterobacteriaceae such as *E. coli.*

DETAILED DESCRIPTION OF THE INVENTION

The present invention relates to the isolation and identification of a nucleic acid which encodes for a hypersensitive response elicitor protein from *Xanthomonas campestris* pv. *pelargonii.* One form of the nucleic acid of the present invention is the hreX gene isolated from *Xanthomonas campestris* pv. *pelargonii,* which has a nucleic acid sequence corresponding to SEQ. ID. No.1 as follows:

```
atggactcta tcggaaacaa cttttcgaat atcggcaacc tgcagacgat gggcatcggg   60
cctcagcaac acgaggactc cagccagcag tcgccttcgg ctggctccga gcagcagctg  120
gatcagttgc tcgccatgtt catcatgatg atgctgcaac agagccaggg cagcgatgca  180
```

-continued

```
aatcaggagt gtggcaacga acaaccgcag aacggtcaac aggaaggcct gagtccgttg  240
acgcagatgc tgatgcagat cgtgatgcag ctgatgcaga accagggcgg cgccggcatg  300
ggcggtggcg gttcggtcaa cagcagcctg ggcggcaacg cc                    342
```

Also suitable as an isolated nucleic acid molecule according to the present invention is an isolated nucleic acid molecule encoding a hypersensitive response elicitor protein, wherein the nucleic acid selectively hybridizes to the DNA of SEQ. ID. No.1 (or its complement) under stringent conditions. Homologous nucleotide sequences can be detected by selectively hybridizing to each other. Selectively hybridizing is used herein to mean hybridization of DNA or RNA probes from one sequence to the "homologous" sequence under stringent conditions which are characterized by a hybridization buffer comprising 2×SSC, 0.1% SDS at 56° C. (Ausubel, et al., Eds., 1989, Current Protocols in Molecular Biology, Vol. I, Greene Publishing Associates, Inc. and John Wiley & Sons, Inc., New York, at page 2.10.3, which is hereby incorporated by reference in its entirety). Another example of suitable stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μg/ml E.coli DNA.

The present invention also relates to the HreX protein, encoded by the nucleotide corresponding to SEQ. ID. NO.1, where the encoded protein has an amino acid sequence corresponding to SEQ. ID. No.2 as follows:

subcloning gene fragments. The subclones then are expressed in vitro or in vivo in bacterial cells to yield a smaller protein or peptide that can be tested for elicitor activity according to the procedure described, e.g., in Wei et al., "Harpin, Elicitor of the Hypersensitive Response Produced by the Plant Pathogen *Erwinia amylovora*," Science 257:85–86 (1992), which is hereby incorporated by reference in its entirety.

As an alternative, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for expression of a truncated peptide or protein.

Chemical synthesis can also be used to make suitable fragments. Such a synthesis is carried out using known

```
Met Asp Ser Ile Gly Asn Asn Phe Ser Asn Ile Gly Asn Leu Gln Thr
 1               5                  10                  15

Met Gly Ile Gly Pro Gln Gln His Glu Asp Ser Ser Gln Gln Ser Pro
                20                  25                  30

Ser Ala Gly Ser Glu Gln Gln Leu Asp Gln Leu Leu Ala Met Phe Ile
            35                  40                  45

Met Met Met Leu Gln Gln Ser Gln Gly Ser Asp Ala Asn Gln Glu Cys
        50                  55                  60

Gly Asn Glu Gln Pro Gln Asn Gly Gln Gln Glu Gly Leu Ser Pro Leu
 65                 70                  75                  80

Thr Gln Met Leu Met Gln Ile Val Met Gln Leu Met Gln Asn Gln Gly
                85                  90                  95

Gly Ala Gly Met Gly Gly Gly Ser Val Asn Ser Ser Leu Gly Gly
            100                 105                 110

Asn Ala
```

This hypersensitive response elicitor protein has an estimated molecular weight of about 12 kDa based on the deduced amino acid sequence. This is consistent with the molecular weight of about 14 kDa as detected by SDS-PAGE (see infra).

Fragments of the above hypersensitive response elicitor polypeptides or proteins are encompassed by the present invention.

Suitable fragments can be produced by several means. In the first, subclones of the gene encoding the hypersensitive response elicitor protein of the present invention are produced by conventional molecular genetic manipulation by amino acid sequences for the elicitor being produced. Alternatively, subjecting a full length elicitor to high temperatures and pressures will produce fragments. These fragments can then be separated by conventional procedures (e.g., chromatography, SDS-PAGE).

Variants may also (or alternatively) be made, for example, by the deletion of addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The protein or polypeptide of the present invention is preferably produced in purified form (preferably at least about 80%, more preferably 90%, pure) by conventional techniques. Typically, the protein or polypeptide of the present invention is secreted into the growth medium of *Xanthomonas* cells or host cells which express a functional type III secretion system capable of secreting the protein or polypeptide of the present invention. Alternatively, the protein or polypeptide of the present invention is produced but not secreted into growth medium of recombinant host cells (e.g., *Escherichia coli*). In such cases, to isolate the protein, the host cell (e.g., *E. coli*) carrying a recombinant plasmid is propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the hypersensitive response elicitor polypeptide or protein of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in sense orientation and correct reading frame. The vector contains the necessary elements for the transcription and translation of the inserted protein-coding sequences. Thus, the present invention also relates to a DNA construct containing the nucleic acid of the present invention, which is operably linked to both a 5' promoter and a 3' regulatory region (i.e., transcription terminator) capable of affording transcription and expression of the encoded HreX protein in host cells or host organisms.

The present invention also relates to an expression vector containing a DNA molecule encoding a hypersensitive response elicitor protein. The nucleic acid molecule of the present invention may be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation.

A variety of vectors are available for stable transformation using *Agrobacterium tumefaciens,* a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant chromosomal DNA. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens.* See Fraley et al., "Expression of Bacterial Genes in Plant Cells," *Proc. Nat'l Acad. Sci.,* 80:4803–4807 (1983), which is hereby incorporated by reference in its entirety.

Other suitable vectors for practicing the present invention include, but are not limited to, the following viral vectors such as lambda vector system gt11, gtWES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology.* 185:60–89 (1990) which is hereby incorporated by reference in its entirety), and any derivatives thereof. Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e. their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promotor, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens*, (U.S. Pat. No. 5,034,322 to Rogers et al., which is hereby incorporated by reference in its entirety), the cauliflower mosaic virus (CaMv) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference in its entirety).

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature* 313(6005):810–812 (1985), which is hereby incorporated by reference in its entirety). Virtually any 3' regulatory region known to be operable in plants would suffice for proper expression of the coding sequence of the DNA construct of the present invention.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual,* Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell.

One approach to transforming plant cells with a DNA construct of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$) To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824-5828 (1985), which is hereby incorporated by reference in its entirety) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference in its entirety). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene. Fraley, et al., *Proc. Natl. Acad. Sci. USA,* 79:1859–63 (1982), which is hereby incorporated by reference in its entirety.

The vector described above can also be microinjected directly into plant cells by use of micropipettes to transfer mechanically the recombinant DNA. Crossway, *Mol. Gen. Genetics,* 202:179–85 (1985), which is hereby incorporated by reference in its entirety. The genetic material may also be transferred into the plant cell using polyethylene glycol. Krens, et al., *Nature,* 296:72–74 (1982), which is hereby incorporated by reference in its entirety.

Another appropriate method of introducing the DNA construct into plant cells to produce stable transformants is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. See, e.g., Horsch et al., Stable transformants can also be generated using Agrobacterium via the "dipping" method, a modification of the vacuum infiltration method as described in Bent et al., "Floral Dip: A Simplified Method for Agrobacterium-Mediated Transformation of *Arabidopsis thaliana,*" *Plant J.* 16:735–43 (1998), which is hereby incorporated by reference in its entirety.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coil* that encodes the β-glucuronidase protein, also known as GUS (Jefferson et al., "GUS Fusions: β Glucuronidase as a Sensitive and Versatile Gene Fusion Marker in Higher Plants," *EMBO Journal* 6:3901–3907 (1987), which is hereby incorporated by reference in its entirety). GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry (Jefferson et al., "GUS Fusions: β Glucuronidase as a Sensitive and Versatile Gene Fusion Marker in Higher Plants," *EMBO Journal* 6:3901–3907 (1987), which is hereby incorporated by reference in its entirety). Other suitable selection markers include, without limitation, markers encoding for antibiotic resistance, such as the nptII gene which confers kanamycin resistance (Fraley, et al., *Proc. Natl. Acad. Sci. USA,* 80:4803–4807 (1983), which is hereby incorporated by reference in its entirety) and the dhfr gene, which confers resistance to methotrexate (Bourouis et al., *EMBO J.* 2:1099–1104 (1983), which is hereby incorporated by reference in its entirety). A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

It is known that practically all plants can be regenerated from cultured cells or tissues, both monocots and dicots.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

The present invention further relates to methods of imparting disease resistance to plants, enhancing plant growth, effecting insect control for plants, and/or imparting stress resistance to plants. These methods involve applying the hypersensitive response elicitor polypeptide or protein of the present invention to all or part of a plant or a plant seed under conditions effective for the polypeptide or protein to impart disease resistance, enhance growth, and/or control insects to the plant or a plant grown from the treated plant seed. Alternatively, the hypersensitive response elicitor protein or polypeptide can be applied to plants such that seeds recovered from such plants themselves are able to impart disease resistance in plants, enhance plant growth, effect insect control, and/or impart stress resistance. AS noted infra, these uses may be beneficial to transgenic plants, either for maximizing the benefit of a transgenic trait of overcoming a yield penalty associated with a transgenic trait.

Another aspect of the present invention relates to a method of imparting post-harvest disease or desiccation resistance to fruits or vegetables. This method involves applying the hypersensitive response elicitor polypeptide or protein of the present invention to all or part of a plant or a plant seed (i.e., before harvesting) or applying this hypersensitive response elicitor to fruits or vegetables after their harvest.

The present invention also relates to methods of inhibiting desiccation of cuttings from ornamental plants, harvesting cuttings from ornamental plants, and promoting early flowering of ornamental plants, using either the DNA molecule(s) of the present invention or proteins or polypeptides encoded by such DNA molecules.

The ornamental plants can be transgenic plants which express a heterologous hypersensitive response elicitor protein or polypeptide of the present invention or the ornamental plants can be treated (i.e., via topical application) with the hypersensitive response elicitor protein or polypeptide of the present invention. Alternatively, the cutting from the ornamental plant (whether transgenic or not) can itself be treated with the hypersensitive response elicitor protein or polypeptide of the present invention, independent of any treatment provided to the ornamental plant from which the cutting is removed.

The embodiments of the present invention where the hypersensitive response elicitor polypeptide or protein is applied to the plant or plant seed (or fruit or vegetable) can be carried out in a number of ways, including: 1) application of an isolated protein or 2) application of bacteria which do not cause disease and are transformed with a gene encoding the protein of the present invention. In the latter embodiment, the protein can be applied to plants or plant seeds by applying bacteria containing the DNA molecule encoding the protein of the hypersensitive response elicitor. Such bacteria are preferably capable of secreting or exporting the protein so that the protein can contact plant or plant seed cells. In these embodiments, the protein is produced by the bacteria in planta, on seeds, on the fruit or vegetable, on cuttings or just prior to introduction of the bacteria to the plants or plant seeds.

The methods of the present invention can be utilized to treat a wide variety of plants or their seeds to impart disease resistance, enhance growth, control insects, impart stress resistance, impart post-harvest disease resistance, inhibit desiccation of cuttings from ornamental plants, and/or promote early flowering of ornamental plants.

Suitable plants include dicots and monocots. More particularly, useful crop plants can include, without limitation: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are, without limitation: *Arabidopsis thaliana,* Saintpaulia, petunia, pelargonium, poinsettia, chrysanthemum, carnation, rose, tulip, and zinnia.

With regard to the use of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus. Resistance, inter alia, to the following bacteria can also be imparted to plants in accordance with present invention: *Pseudomonas* spp., and *Xanthomonas* spp., and *Erwinia* spp. Plants can be made resistant, inter alia, to the following fungi by use of the method of the present invention: *Fusarium* spp., *Phytophthora* spp., *Alternaria* spp., and *Botrytis* spp. Imparting pathogen resistance to plants using hypersensitive response elicitors is disclosed in WO 96/39802 to Wei et al. and WO 98/24297 to Qiu et al., which are hereby incorporated by reference in their entirety.

With regard to the use of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased percentage of seeds germinated, increased plant size, greater biomass, more and bigger fruit, earlier fruit coloration, earlier flower opening, improved flower longevity (i.e., shelf-life), and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land. Imparting enhanced growth to plants using hypersensitive response elicitors is disclosed in detail in WO 98/32844 to Qiu et al., which is hereby incorporated by reference in its entirety.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection. The use of hypersensitive response elicitors to promote insect control on plants is disclosed in detail in WO 98/37752 to Zitter et al., which is hereby incorporated by reference in its entirety.

The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, tomato pinworm, and maggots. Collectively, this group of insect pests represents the most economically important group of pests for vegetable production worldwide.

The hypersensitive response elicitor protein or polypeptide of the present application can be used to inhibit or otherwise control post-harvest diseases (i.e., caused by pathogens) in fruits or vegetables. Likewise, such treatment can also inhibit post-harvest desiccation of treated fruits or vegetables. In achieving these objectives, the present invention enables produce growers, warehouse packers, shippers, and suppliers to process, handle, and store fruits and vegetables with reduced losses caused by post-harvest disease and desiccation. As a result, the cost of bringing fruits and vegetables from the field to the consumer can be reduced. Importantly, the quality of the treated fruits and vegetables is improved. The use of hypersensitive response elicitors to inhibit post-harvest disease and/or desiccation of fruits or vegetables is disclosed in U.S. Provisional Patent Application Serial No. 60/198,359 to Wei et al., filed Apr. 19, 2000, which is hereby incorporated by reference in its entirety.

Another aspect of the present invention is directed to imparting stress resistance to plants. Stress encompasses any enviromnental factor having an adverse effect on plant physiology and development. Examples of such environmental stress include climate-related stress (e.g., drought, water, frost, cold temperature, high temperature, excessive light, and insufficient light), air pollution stress (e.g., carbon dioxide, carbon monoxide, sulfur dioxide, $NO_x$, hydrocarbons, ozone, ultraviolet radiation, acidic rain), chemical (e.g., insecticides, fungicides, herbicides, heavy metals), and nutritional stress (e.g., fertilizer, micronutrients, macronutrients). Use of the hypersensitive response elicitor in accordance with the present invention imparts resistance to plants against such forms of environmental stress. The use of hypersensitive response elicitors to impart stress resistance to plants is disclosed in U.S. patent application Ser. No. 09/431,614 to Wei et al., filed Nov. 2, 1999, which is hereby incorporated by reference in its entirety.

Another aspect of the present invention is a method carried out by providing a plant or plant seed including a transgene conferring a transgenic trait to the plant or a plant grown from the plant seed, and then applying to the plant or plant seed a hypersensitive response elicitor protein or polypeptide of the present invention. By applying the hypersensitive response elicitor to the plant or plant seed, enhanced growth, stress tolerance, disease resistance, or insect resistance can be imparted to transgenic plants. According to one embodiment, the applying of the hypersensitive response elicitor is carried out under conditions effective to impart enhanced growth, stress tolerance, disease resistance, or insect resistance to the plant or the plant grown from the plant seed, thereby maximizing the benefit of the transgenic trait to the plant or the plant grown from the plant seed. For example, when the particular value-added trait relates to specific but limited growth enhancement, stress tolerance, disease resistance, or insect resistance of a transgenic plant, this embodiment relates to providing broad growth enhancement, stress tolerance, disease resistance, or insect resistance that complements the specific but limited value-added trait. According to another embodiment, the transgenic trait is associated with a deleterious effect on growth, stress tolerance, disease resistance, or insect resistance in the transgenic plant and the applying of the hypersensitive response elicitor is carried out under conditions effective to impart enhanced growth, stress tolerance, disease resistance, or insect resistance to the plant or the plant grown from the plant seed, thereby overcoming the deleterious effect. Thus, this aspect of the present invention is directed to overcoming a yield penalty resulting from a value-added trait.

Another aspect of the present invention is a method which is carried out by providing a plant cell; transforming the plant cell with (i) a first DNA molecule encoding a transcript or a protein or polypeptide which confers a trait to a plant grown from the transformed plant cell and (ii) a second DNA molecule encoding a hypersensitive response elicitor protein or polypeptide of the present invention, which is different than the protein or polypeptide encoded by the first DNA molecule, the transforming being carried out under conditions effective to produce a transformed plant cell; and then regenerating a transgenic plant from the transformed plant cell. By transforming the plant cell with the second DNA molecule encoding the hypersensitive response elicitor protein or polypeptide of the present invention, the resulting transgenic plant expresses the hypersensitive response elicitor and exhibits enhanced growth, stress tolerance, disease resistance, or insect resistance. According to one embodiment, transforming with the second DNA molecule imparts enhanced growth, stress tolerance, disease resistance, or insect resistance to the plant, thereby maximizing benefit to the plant of the trait conferred by transforming with the first DNA molecule. For example, when the particular trait conferred by the first DNA molecule relates to specific but limited growth enhancement, stress tolerance, disease resistance, or insect resistance of a transgenic plant, this embodiment relates to conferring broad growth enhancement, stress tolerance, disease resistance, or insect resistance that complements the specific but limited trait. According to another embodiment, transforming with the first DNA molecule is accompanied by a deleterious effect on growth, stress tolerance, disease resistance, or insect resistance, and transforming with the second DNA molecule overcomes the deleterious effect. Thus, this aspect of the present invention is also directed to overcoming a yield penalty resulting from a trait.

The transgene or DNA molecule conferring a trait can be any DNA molecule that confers a value-added trait to a transgenic plant. The value-added trait can be for disease resistance, insect resistance, enhanced growth, herbicide resistance, stress tolerance, male sterility, modified flower color, or biochemically modified plant product. Biochemically modified plant products can include, without limitation, modified cellulose in cotton, modified ripening of fruits or vegetables, modified flavor of fruits or vegetables, modified flower color, expression of industrial enzymes, modified starch content, modified dietary fiber content, modified sugar metabolism, modified food quality or nutrient content, and bioremediation.

The transgene or DNA molecule conferring a value-added trait can encode either a transcript (sense or antisense) or a protein or polypeptide which is different from the hypersensitive response elicitor protein or polypeptide. Either the transcript or the protein or polypeptide, or both, can confer the value-added trait.

A number of proteins or polypeptides which can confer a value-added trait are known in the art and others are continually being identified, isolated, and expressed in host plants. Suitable proteins or polypeptides which can be encoded by the transgene or DNA molecule conferring a value-added trait include, without limitation, B.t. toxin, *Photorhabdus luminescens* protein, protease inhibitors, amylase inhibitors, lectins, chitinases, endochitinase, chitobiase, defensins, osmotins, crystal proteins, virus proteins, herbicide resistance proteins, mannitol dehydrogenase, PG inhibitors, ACC degradation proteins, barnase, phytase, fructans, invertase, and SAMase.

A number of transcripts which can confer a value-added trait are known in the art and others are continually being identified, isolated, and expressed in host plants. The transcript encoded by the transgene or DNA molecule conferring a trait can be either a sense RNA molecule, which is translatable or untranslatable, or an antisense RNA molecule capable of hybridizing to a target RNA or protein. Suitable transcripts which can be encoded by the transgene or DNA molecule conferring a trait include, without limitation, translatable and untranslatable RNA transcripts capable of interfering with plant virus pathogenesis (de Haan et al., "Characterization of RNA-Mediated Resistance to Tomato Spotted Wilt Virus in Transgenic Tobacco Plants," *BioTechnology* 10:1133–1137 (1992); Pang et al., "Nontarget DNA Sequences Reduce the Transgene Length Necessary for RNA-Mediated Tospovirus Resistance in Transgenic Plants," *Proc. Natl. Acad. Sci. USA* 94:8261–8266 (1997), which are hereby incorporated by reference in their entirety) and antisense RNA molecules which interfere with the activity of an enzyme (e.g., starch synthase, ACC oxidase, pectinmethylesterase, polygalacturonase, etc.) or the synthesis of a particular product (e.g., glycoalkaloid synthesis).

With the attendant benefits of applying the hypersensitive response elicitor of the present invention to a transgenic plant or plant seed, or heterologously expressing the hypersensitive response elicitor of the present invention in the transgenic plant, the effectiveness of a transgenic plant is improved (i.e., maximum benefit is realized or the yield penalty is overcome). The use of hypersensitive response elicitors for the purpose of maximizing the benefit of a transgenic trait or overcoming a concomitant yield penalty is disclosed in U.S. Provisional Patent Application Serial No. 60/211,585 to Wei et al., filed Jun. 15, 2000, which is hereby incorporated by reference in its entirety.

The methods of the present invention can also be utilized to treat a wide variety of ornamental plants to control desiccation of cuttings removed therefrom as well as promoting early blooming of flowers and enhancing the longevity of flower blooms. Cuttings include stems, leaves, flowers, or combinations thereof. With respect to desiccation, complete protection against desiccation may not be conferred, but the severity of desiccation can be reduced. Desiccation protection inevitably will depend, at least to some extent, on other conditions such as storage temperatures, light exposure, etc. However, this method of controlling desiccation has the potential for eliminating some other treatments (i.e., additives to water, thermal regulation, etc.), which may contribute to reduced costs or, at least, substantially no increase in costs. The use of hypersensitive response elicitors to impart resistance against desiccation of cuttings, promoting earlier flowering of blooms, and promoting the longevity of flower blooms is disclosed in U.S. Provisional Patent Application Serial No. 60/248,169, filed Nov. 13, 2000, to Wei et al., which is hereby incorporated by reference in its entirety.

The method of the present invention involving application of the hypersensitive response elicitor polypeptide or protein of the present invention, can be carried out through a variety of procedures when all or part of the plant is treated, including flowers, leaves, stems, roots, propagules (e.g., cuttings), fruits or vegetables, etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds or propagules (e.g., cuttings), in accordance with the application embodiment of the present invention, the hypersensitive response elicitor protein or polypeptide, in accordance with present invention, can be applied by low or high pressure spraying, coating, immersion, or injection. Other suitable application procedures can be envisioned by those skilled in the art provided they are able to effect contact of the protein with cells of the plant, plant seed, or fruit or vegetable. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide or whole elicitors to impart disease resistance to plants, enhance plant growth, control insects, and/or impart stress resistance to plants. As noted above, either pre-harvest treatment of plants or post-harvest treatment of fruits or vegetables can impart post-harvest disease or desiccation resistance to the fruits or vegetables.

The hypersensitive response elicitor polypeptide or protein, in accordance with the present invention, can be applied to plants, plant seeds, plant cuttings, or fruits or vegetables alone or in a mixture with other materials. Alternatively, the polypeptide or protein can be applied separately to plants, plant seeds, plant cuttings, or fruits or vegetables, with other materials being applied at different times.

A composition suitable for treating plants, plant seeds, plant cuttings, or fruits or vegetables in accordance with the application embodiment of the present invention contains a hypersensitive response elicitor polypeptide or protein derived from *Xanthomonas campestris* pv. *pelargonii*. Suitable carriers include water, aqueous solutions, slurries, or dry powders. In this embodiment, the composition contains greater than about 5 nM of the protein of the present invention.

Although not required, this composition may contain additional additives including fertilizer, insecticide, fungicide, nematicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and, in some instances, abrading agents. These materials can be used to facilitate the process of the present invention. In addition, the hypersensitive response eliciting protein can be applied to plant seeds with other conventional seed formulation and treatment materials, including clays and polysaccharides.

In the alternative embodiment of the present invention involving the use of transgenic plants and transgenic seeds, a hypersensitive response elicitor need not (but may) be applied topically to the plants, plant seeds, plant cuttings, or harvested fruits or vegetables. Instead, transgenic plants transformed with a DNA molecule encoding such a protein are produced according to procedures described above and well known in the art. The applied hypersensitive response elicitor need not be the same hypersensitive response elicitor expressed heterologously by the plant. A number of other hypersensitive response elicitors are known, including but not limited to those isolated from *Erwinia* spp., *Pseudomonas* spp., *Clavibacter* spp., and *Phytophthora* spp.

The following examples are intended to illustrate, but by no means are intended to limit, the scope of the present invention as set forth in the appended claims.

EXAMPLES

Example 1

Cell-Free-Elicitor-Preparation

The first step in the identification and purification of the *Xanthomonas campestris* pv. *pelargonii* hypersensitive response elicitor (Xcp HR elicitor) was the development of a cell-free-elicitor-preparation, or CFEP. CFEP production involved culture growth, sonication of the resuspended cell pellet, and heat treatment of the sonicate.

1. Culture Growth

*Xanthomonas campestris* pv. *pelargonii* (Xcp) was grown on plates containing LA. Seed cultures were inoculated from these plates and grown in 50% LB at approximately 27° C. (room temperature), until an optical density ($OD_{620}$) of 0.5 to 0.8 was achieved. The seed cultures were then used to inoculate minimal media cultures in a manner such that no LB was introduced into the minimal media. A 1:10 ratio of seed culture to minimal media was used to inoculate into the minimal media cultures (i.e. the cell pellet from a 50 ml seed culture was used to inoculate 500 ml of minimal media). The minimal media culture was grown at approximately 27° C. (room temperature) until an $OD_{620}$ of 1.7 to 2.0 was achieved.

After culture growth in flasks had been optimized, fermentation was transferred to a 10 L fermentor. The fermentation was run at approximately 270° C. with an initial pH of 6.0 and a final pH of 5.8. The vessel was agitated at 400 rpm with 0.8 to 1.0 vessel volumes of air per minute.

Growth of Xcp in the minimal media served to induce the bacteria to produce significant amount of the HR elicitor. A 1 L 10×stock solution of the minimal media contained 39.2 g of $K_2HPO_4$, 71.5 g $KH_2PO_4$, 10.0 g of $(NH_4)_2SO_4$, 3.5 g of $MgCl_2$, 1.0 g of NaCl, and 34.23 g of sucrose (Huynh et al., "Bacterial Blight of Soybean: Regulation of a Pathogen Gene Determining Host Cultivar Specificity," *Science* 245, 1374 (1986) which is hereby incorporated by reference in its entirety). The final pH of the media stock was 6.0 to 6.2. After thoroughly mixing, the stock was sterile filtered and stored at 4° C.

2. Sonication

Once the desired OD was reached, the minimal media culture was centrifuged. The resulting cell pellet was resuspended at a 1:10, weight to volume ratio in lysis buffer (20 mM NaCl and 20 mM Tris-HCl at pH 8.0). The resuspended cells were ruptured by sonication. The resulting sonicate was maintained on ice until the heat-treatment.

3. Heat Treatment

The sonicate was placed on a preheated stir plate, and brought to a rolling boil. The boil was maintained for 5 minutes. The solution was then placed in an ice water bath and cooled to approximately 10° C.

Once cooled the sonicate was brought back to its original volume with deionized $H_2O$ (replacing the volume lost to evaporation during boiling). The solution was then centrifuged at 31000×g for 30 minutes. The resulting supernatants were combined and frozen at −80° C.

Example 2

Elicitor-Induced Hypersensitive Response

The Xcp HR elicitor CFEP was infiltrated into several plants for HR analysis. The CFEP induced HR in species of tobacco, tomato, and bean. It did not induce HR in geranium, the host organism of *Xanthomonas campestris* pv. *pelargonii*.

Example 3

Protein Verification

To confirm that the Xcp HR elicitor was a protein, protease digestions were performed with HR active CFEP.

CFEP was inoculated with proteinase at a concentration of 2 mg/ml. After incubation at 37° C., the protease inoculated CFEP along with the positive control (CFEP alone) and negative control (protease K at 2 mg/ml in lysis buffer) were infiltrated into tobacco plants. The proteinase inoculated CFEP showed no signs of HR. The positive control showed symptoms of HR, the negative control showed no signs of HR. These results indicated that the Xcp HR elicitor was sensitive to protease digestion and therefore a protein. This experiment was repeated several times with different batches of CFEP, each time with the same results.

Example 4

Chromatographic Purification

Further purification of the Xcp HR elicitor was achieved using chromatographic techniques. After screening a wide range of chromatographic medias, a purification scheme based on hydrophobic interaction and cation exchange chromatography was designed. All chromatographic procedures were conducted using a FPLC system (Pharmacia Biotech, Piscataway, N.J.).

1. Butyl Sepharose

CFEP was first bound to a medium strength hydrophobic interaction chromatography medium. CFEP was adjusted to 600 mM NaCl and loaded onto a Butyl Sepharose 4 Fast Flow column (Pharmacia Biotech, Piscataway, N.J.). The column was eluted with a 75–100% B gradient. Buffer A contained 600 mM NaCl, 20 mM Tris-HCl pH 8. Buffer B contained 10 mM Tris-HCl pH 8. The HR active fraction eluted at approximately 100% B.

2. Mono S

Fractions from the Butyl Sepharose column determined to contain high concentration of the HR elicitor (determined by HR activity) were pooled and loaded onto a strong cation exchanger, Mono S (Mono S 10/10 column, Pharmacia Biotech, Piscataway, N.J.). Prior to loading, the sample was adjusted to 20 mM NaCl, 20 mM Tris-HCl pH 5.5. Buffer A contained 20 mM NaCl, 20 mM Tris-HCl pH 5.5. Buffer B contained 1M NaCl, 20 mM Tris-HCl pH 5.5. The column was washed and a single step elution to 100% B was performed. The HR elicitor did not bind to the Mono S medium, but at pH 5.5 many of the contaminates in the sample did bind. Immediately following the collection of the flow through (the HR active fraction) was adjusted to pH 8.0.

3. Phenyl Sepharose

The active fraction from the Mono S column was loaded onto a Phenyl Sepharose 6 Fast Flow Low Substitution column (a weak hydrophobic interaction medium, Pharmacia Biotech, Piscataway, N.J.). Buffer A contained 1 M NaCl, 20 mM Tris-HCl pH 8, and buffer B contained 10 mM Tris-HCl pH 8.0. The HR active fraction eluted at approximately 100% B.

4. Analysis

At this stage the HR elicitor had been identified and purified to near homogeneity.

Example 5

Xcp HR Elicitor Biochemical Characteristics

The HR elicitor was determined, by SDS-PAGE, to be approximately 14 kDa with an approximate pI of 4. (This molecular weight determination by SDS-PAGE is consistent with the approximately 12 kDa molecular weight estimation based on the deduced amino acid sequence.) The most troublesome characteristic of the Xcp HR elicitor was its abnormal staining characteristics on SDS-PAGE. Under normal loading conditions when a SDS-PAGE was stained and destained with Coomassie blue techniques, the HR elicitor was not visible. The elicitor was temporarily visible with Coomassie blue staining only when the gel was extensively overloaded. Visualization of the elicitor was achieved with copper and silver staining techniques. In the case of silver staining the elicitor band either appeared as a negatively stained band with relatively distinct borders (at higher concentration) or as an off-colored band with undefined borders.

Example 6

Amino Acid Sequence of the Xcp Hypersensitive Response Elicitor

A proteolytic digestion of the purified hypersensitive response elicitor was performed followed by a peptide separation. Amino acid sequencing of one of the peptides yielded a very strong unambiguous sequence of nine amino acids. The amino acid sequence was as follows: aspartate, serine, isoleucine, glycine, asparagine, asparagine, phenylalanine, serine, asparagine (amino acid residues 2–10 of SEQ. ID. No.2).

Example 7

Elicitor-Induced Disease Resistance in Tobacco

Tobacco plants were treated with the Xcp HR elicitor. Three days after the treatment, the plants were inoculated with tobacco mosaic virus (TMV). Four days after TMV inoculation the elicitor treated plants showed a 75% reduction of TMV caused lesions compared to the untreated control plants.

Example 8

Elicitor-Induced Growth Enhancement of Tomato

Tomato seeds were soaked in solution containing the Xcp HR elicitor for more than four hours. Seeds soaked in the same solution without the elicitor served as a control. The elicitor treated plants were observed to have 15–20% greater average growth than the control plants (measured in plant height from 12 plants).

Example 9

Construction of Genomic Library

*Xanthomonas campestris* pv. *pelargonii* genomic DNA was purified and then partially digested with a restriction enzyme. DNA fragments of the desired size were isolated and then ligated into a prepared vector. The constructs were transduced into *E. coli* competent cells. The newly constructed library was analyzed with regard to its background and insert heterogeneity.

1. Isolation of Genomic DNA

Cultures of *Xanthomonas campestris pelargonii* were grown in LB at room temperature to an approximate $OD_{620}$ of 5.0. DNA was isolated from the cultures by a procedure based on a protocol from Experiments With Gene Fusion (pp. 137), and modified by D. Bauer. The cells were lysed with lysozyme followed by a proteinase and an RNase treatment. The DNA was extracted several times with phenol/chloroform/isoamyl alcohol and chloroform/isoamyl alcohol. Following this procedure the genomic DNA was further purified by a cesium chloride-ethidium bromide separation technique described in Sambrook et al., *Molecular Cloning: A Laboratory Manual,* Cold Springs Laboratory, Cold Springs Harbor, N.Y. (1989), which is hereby incorporated by reference in its entirety. After removal of the ethidium bromide the genomic DNA was quantified and stored at −80° C.

2. Partial Digestion of Genomic DNA

The isolated genomic DNA was partially digested to generate DNA fragments of 9000 to 12000 bp in length. The restriction enzyme Sau3A1 was used for the partial digestion of the DNA. Pilot experiments were run to determine optimal proportions of DNA to enzyme in order to generate the highest concentrations of DNA fragments of the desired length. After optimization was completed a large-scale partial digestion was conducted. The digestions were run on an agarose gel and stained with ethidium bromide. The DNA fragments between 9000 to 12000 bp were excised from the gel. The DNA fragments were then electroeluted from the agarose gel using an EluTrap column (Schleicher & Schuell, Keene, N.H.). In this manner a large pool of genomic DNA fragments of the desired length was generated and purified.

3. Library Vector Preparation

The vector used for the library was pBluescript II KS+ (Stratagene, La Jolla, Calif.). The vector was digested with BamHI, a restriction enzyme generating cohesive ends that are compatible with DNA digested with Sau3A1. The digested vector was dephosphorylated with calf intestinal alkaline phosphatase (CIAP). Prior to use in ligation reactions the digested and dephosphorylated vector was run on a low-melting temperature agarose gel, excised from the gel and extracted using an S&S Elu-Quick DNA Purification Kit (Schleicher & Schuell, Keene, N.H.). This procedure yielded a purified pBluescript II KS+ vector that was ready to accept the genomic DNA inserts.

4. Ligation and Transformation

The prepared vector and inserts were ligase treated using T4 DNA ligase and a procedure described by the manufacturer's instructions and as described in Sambrook et al., *Molecular Cloning: A Laboratory Manual,* Cold Springs Laboratory, Cold Springs Harbor, N.Y. (1989), which is hereby incorporated by reference in its entirety. The resulting constructs were then transduced into *E. coli* MAX Efficiency DH5α F'IQ Competent Cells (Gibco BRL/Life Technologies, Rockville, Md.) following the manufacturer's instructions.

5. Library Analysis

The library was analyzed with regard to its background (individuals in the library not containing an insert) and for heterogeneity among the inserts present in the library. Twenty-five to thirty percent of the constructs present in the library were determined to be background by blue/white color selection (as determined by IPTG induction in the presence of X-gal). The heterogeneity of the library was determined by plating the library, randomly selecting colonies, isolating the plasmids from the randomly chosen colonies, and digesting them with BamHI. The digested colonies were then analyzed on an agarose gel. Of the colonies containing inserts, none of them displayed identical patterns of digested DNA fragments. This is a strong indicator that all of the colonies tested contained different genomic inserts and therefore that the library was constructed from a diverse range of Xcp genomic DNA fragments. The library was designated Xcp Lib. II.

Example 10

Oligonucleotide Probe

Pools of oligonucleotide were designed such that when combined they generated a fully degenerated pool of oligonucleotide that coded for the amino acid sequence described in Example 6 (i.e., amino acid residues 2–10 of SEQ. ID. No.2). Prior to use as a probe in colony and southern hybridizations, the degenerate pool of oligonucleotides was radioisotope labeled via a phosphorylation reaction. T4 Polynucleotide Kinase was used to phosphorylate the 5' end of the oligonucleotides with $[Y^{32}P]ATP$ (Sambrook et al., *Molecular Cloning: A Laboratory Manual,* Cold Springs Laboratory, Cold Springs Harbor, N.Y. (1989), which is hereby incorporated by reference in its entirety).

Example 11

Colony Hybridization

The Xcp genomic library described above was plated and the DNA from each colony immobilized onto nylon membranes. The membranes were blocked and hybridized at a specific temperature in the presence of the labeled probe. The membranes were then washed to remove excess probe and exposed to autoradiography film. After exposure, the film showed distinct spots or signals where the labeled probe had hybridized to complementary sequences of genomic DNA contained in the library.

1. Colony Lift

Dilutions of the Xcp Lib II library were made and spread onto 150 mm diameter plates containing LA. Approximately 7000 colonies were screened; 10 plates each containing 700 colonies. Colony lifts were made using a positively charged nylon membrane (Hybond NX, Amersham Pharmacia, Piscataway, N.J.). After the colony lifts were made, the membranes were saturated with 10% SDS to lyse the cells. The membranes were then saturated with denaturing solution (0.5 M NaOH, 1.5 M NaCl), neutralization solution (1.5 M NaCl, 1 M Tris-HCl pH 8), and rinsed with 2×SSC. The cell debris was removed from the membrane by incubating the membranes with 2 mg/ml of Proteinase (Qiagen, Valencia, Calif.) and rinsing them in 99% ethanol. The membranes were dried and the DNA was fixed to the membrane via a UV crosslinker.

2. Prehybridization and Hybridization

Prehybridization and hybridization were conducted in Seal-A-Meal bags containing 75 ml of solution. The prehybridization solution contained 3M TMAC (tetramethylammoniumchloride), 100 mM $NaPO_4$, 1 mM EDTA, 5×Denhardts solution, 0.6% SDS, in MilliQ water. The membranes were prehybridized on a rocking platform for approximately 3 hours at 47° C. The prehybridization solution was exchanged for hybridization solution and hybridized on a rocking platform for approximately 62 hours at 47° C. The hybridization solution was identical to the prehybridization solution with the addition of approximately 30 pmol of labeled probe (described in Example 10).

3. Membrane Wash

The wash solution consisted of 3 M TMAC, 50 mM Tris-HCl pH 8, 0.2% SDS in MilliQ water. Membranes were removed from the hybridization bag and rinsed in wash solution for 5 minutes at room temperature on a rotary shaker. The wash solution was exchanged and the membranes were washed under the same conditions for 20 minutes. The membranes were then washed on a rocking platform at 47° C. in pre-equilibrated wash solution for 1 hour. The membrane wash concluded with a final rinse with 2×SSC, 0.1% SDS.

4. Membrane Exposure and Development

Following the membrane wash, the membranes were wrapped in plastic wrap and exposed. Membranes were exposed to Kodak BioMax MS film (Eastman Kodak, Rochester, N.Y.) in the presence of an amplification screen at −80° C. for approximately 16 hours. A Kodak X-OMAT 1000A processor (Eastman Kodak, Rochester, N.Y.) was used to develop the exposure.

5. Analysis

Approximately 12 colonies showed positive hybridization. Twenty-nine colonies were actually isolated from the plates. If the signal from the exposure appeared as if it might have resulted from one of several colonies, all the colonies in question were isolated.

Example 12

Southern Analysis of Clones from Genomic Library

Plasmids from positive hybridizing colonies were isolated. The plasmids were digested, run on an agarose gel and the DNA transferred to a nylon membrane. The membrane was hybridized with the Xcp HR elicitor probe. Hybridization temperatures were manipulated to achieve a high degree of stringency. Positively hybridizing colonies and the exact digestion fragments containing sequences homologous to the probe were identified.

1. Plasmid Isolation and Digestion

The colonies isolated from the colony hybridization experiment were grown in liquid cultures overnight at 37° C. Plasmids were isolated from these cultures using an alkaline extraction miniprep procedure. Included in this procedure was a negative control consisting of *E. coli* DH5α F'IQ with pBluescriptII KS+ (containing no insert). The plasmids were digested with the restriction enzyme BssH II. The digests were then run on an agarose gel stained with ethidium bromide and photographed.

2. Gel Treatment and DNA Transfer

Gel treatment consisted of three steps depurination, denaturation, and neutralization. Between each step the gel was rinsed twice in MilliQ water. All steps were performed on a rotary shaker. The depuration step (0.2 N HCl in MilliQ water) lasted 10 minutes. The denaturation (1.5 M NaCl, 0.5 M NaOH, in MilliQ water) lasted 45 minutes, and the neutralization (1.5 M NaCl, 1 M Tris-HCl pH 7.4) step lasted 30 minutes. The gel was rinsed in 2×SSC in Mill Q water until the transfer was started. The DNA transfer was conducted as described by Sambrook et al., *Molecular Cloning: A Laboratory Manual,* Cold Springs Laboratory, Cold Springs Harbor, N.Y. (1989), which is hereby incorporated by reference in its entirety. The transfer procedure was an upward transfer of the DNA from the gel to a nylon membrane using 10×SSC as the transfer buffer. As with the colony hybridization, the Hybond NX membrane was used (Amersham Pharmacia, Piscataway, N.J.). At completion of the transfer, the membrane was dried and fixed by UV crosslinking.

3. Southern Hybridization

Prehybridization and hybridization were conducted in hybridization tubes with 25 ml of solution. Hybridizations were carried out at 47° C., 51° C., and 59° C. The prehybridization solution, hybridization solution, and the probe were identical to that described during the colony hybridization. Approximately 10 pmol of freshly labeled probe was used in each tube. Prehybridization was conducted for approximately 3 hours and hybridization for approximately 65 hours. Each membrane, with respect to its hybridization temperature, was washed as described during the colony hybridization. Membranes were exposed for 15 hours to Kodak BioMax MS film (Eastman Kodak, Rochester, N.Y.).

4. Analysis

Nine out of the 29 plasmids isolated showed positive hybridization with the HR elicitor probe. It was also possible to determine which of the digestion fragments from each plasmid was actually hybridization with the probe. The negative control (pBluescriptII KS+ with no insert) showed no hybridization.

Example 13

Construction and Southern Analysis of Subclones from Genomic Library

This phase of the project subcloned the positively hybridizing digestion fragments identified in the previous section. A final Southern analysis was preformed to confirm which subclone contained the region homologous to the Xcp HR elicitor probe.

1. Construction of Subclones

Three of the positive hybridizing plasmids from Example 12 were selected for subcloning. Aliquots from the BssH II digested clones were blunt-ended using T4 DNA Polymerase. The blunt-ended digestion reactions were then analyzed on a low melting temperature agarose gel, stained, and photographed. Three of the potentially hybridizing digest fragments from each of the clones were excised from the gel and extracted using a Qiagen Gel Extraction Kit (Qiagen, Valencia, Calif.). The blunt-ended digestion fragments were then ligated to EcoR V digested pBluescript II KS+ (the vector had been previously dephosphorylated with calf intestinal alkaline phosphatase and isolated from a gel.). The ligase treated constructs were transduced into *E. coli* DH5α Subcloning Efficiency Competent Cells (Gibco BRL/Life Technologies, Rockville, Md.).

2. Southern Analysis of Subclones

The subclones were digested with BssH II, run on a gel, transferred, and hybridized as described in the previous sections. Hybridizations and washes were conducted at 51 ° C. Exposure and development were conducted as described in the pervious sections.

3. Analysis

One subclone from each of the original plasmids showed positive hybridization with the HR elicitor probe. The positively hybridizing inserts were between 1500 and 3000 bp in length. The subclones were designated pE156, pE160, and pE162.

Example 14

DNA Sequencing and Gene Identification

Sequencing was conducted using the ABI Prism BigDye Terminator Cycle Sequencing Ready Reaction Kit (PE Biosystems, Foster City, Calif.). The T3 and T7 promoter sites present in the pBluescript II KS+ vector were used for the initial round of sequencing for the pE156, pE160, and pE162 subclones. In the first round of sequencing an exact match of the Xcp HR elicitor probe was identified. Additional primers were made based on the sequences obtained. The primer used to obtain the complete hreX gene sequence, designated primer SP01, is characterized by the nucleotide sequence of SEQ. ID. No.3 as follows:

gatcttgccg ttgcagcttt                                    20

The primer anneals approximately 60 bp upstream of the hreX gene. The second round of sequencing resulted in the identification of an open reading frame (ORF) (SEQ. ID. No.1) that initiated with an ATG start codon, and ended with a stop codon 342 base pairs downstream. The ORF (SEQ. ID. No.1) was found to encode a 114 amino acid protein (SEQ. ID. No.2). The protein has a deduced molecular weight of 11.9 kDa, a theoretical pI of 3.5, and is glycine rich. These characteristics match those of the originally purified Xcp HR elicitor protein. The ORF was designated hreX.

approximately 24 hours after infiltration. HR was observed in CFEP dilutions greater than 1:2000.

Example 17 hreX Homologue Search in Various Bacterial Species

The hreX gene was used as a probe to screen various species of *Xanthomonas* and other bacteria for the presence of an hreX homologue. The probe which was used for Southern analysis is characterized by a nucleotide sequence according to SEQ. ID. No.6 as follows:

```
aattcggctt taccatatgt atccagttca accacatgag acgggaatca ccatgggctc    60
tatcggaaac aacttttcgaatatcggcaa cctgcagacg atgggcatcg ggcctcagca   120
acacgaggac tccagccagc agtcgccttc ggctggctcc gagcagcagc tggatcagtt   180
gctcgccatg ttcatcatga tgatgctgca acagagccag ggcagcgatg caaatcagga   240
gtgtcrgcaac gaacaaccgc agaacggtca acaggaaggc ctgagtccgt tgacgcagat   300
gctgatgcag atcgtgatgc agctgatgca gaaccagggc ggcgccggca tgggcggtgg   360
cggttcggtc aacagcagcc tggcggcaa cgccggatcc ttaagccg               408
```

Example 15

Construction of a High Expression HreX Vector

PCR primers were designed to amplify the hreX gene and introduce a restriction enzyme digest site at the amino terminal and carboxyl terminal regions of the gene. These primers, designated XcpCP02 and XcpCP03, are characterized by the following nucleotide sequences:

XcpCP02, SEQ. ID. No.4 tagcatatgg actctatcgg aaacaactttt t                      31

XcpCP03, SEQ. ID. No.5 aaggatcctc aggcgttgcc gcccaggctg ctg                     33 where the underlined regions correspond to portions of the hreX sequence of SEQ. ID. No. 1.

The gene was PCR amplified and cloned into a pT-Adv vector (AdvanTage PCR Cloning Kit, Clonetech). The plasmid insert was sequenced and confirmed to be an exact representation of the hreX gene. The hreX gene was then restriction digested, isolated from the pT-Adv vector and ligated into a high expression vector. The high expression vector used was pSE111, a variation of the pSDHP1 vector used to express the hrpN gene product, harpin$_{Ea}$. The HreX expression vector was designated pE172, the structure of which is illustrated in FIG. 1.

Example 16

HreX Induced Hypersensitive Response

Expression vector pE172 was grown in *E. coli* DH1 under inducing conditions and culture processed to make a cell-free-elicitor-preparation (as described in Example 1). Dilutions of the HreX CFEP was made and infiltrated into tobacco. Plants were evaluated for symptoms of HR The underlined portion of the probe sequence represents the ORF of the hreX gene and the italicized portion of the probe sequence represent the non-coding region immediately upstream on hreX.

Genomic DNA was isolated from the bacteria strains of interest. The DNA was then digested, run on an agarose gel and transferred to a membrane. The membrane was hybridized with the radioisotope labeled hreX gene.

1. Isolation and Digestion of Genomic DNA

The procedure used for the isolation of genomic DNA was based on procedures described in Experiments with Gene Fusion (pp.137) and Current Protocols in Molecular Biology (pp. 2.4.1) and modified by D. Bauer. The bacterial species of interest were grown at room temperature on a rotary shaker for approximately 48 hour. The cells were lysed with lysozyme followed by a proteinase and an RNase treatment. The DNA was extracted several times with phenol/chloroform/isoamyl alcohol and chloroform/isoamyl alcohol. The resulting isolated genomic DNA was then digested with the restriction enzymes Hind III and BssH II.

2. Preparation and Labeling of the HreX Probe

The hreX gene was restriction digested from the pT-Adv vector, as previously described in Example 15. The digest was run on an agarose gel. The band correlating to the hreX gene was isolated from the gel and extracted using a Qiagen Gel Extraction Kit (Qiagen, Valencia, Calif.). The extracted gene was labeled using a random-primer labeling method (Prime-Ti Rmt Random Primer Labeling Kit, Stratagene, La Jolla, Calif.).

3. Southern Hybridization

The digested genomic DNA was run on an agarose gel (the same approximate amount of digested genomic DNA was run in each lane of the gel), treated and transferred to a nylon membrane, as described earlier sections. The prehybridization solution consisted of 500 mM NaPO$_4$ pH 7.0, 1 mM EDTA, 1.0% BSA Fraction V (weight:volume), 7.0% SDS, in MilliQ water (Church et al., "Genomic Sequencing," *Proc. Nat'l Acad. Sci. USA* 81:1991–1995

(1984) which is hereby incorporated by reference in its entirety). The hybridization solution was identical to the prehybridization solution except that it contained the labeled hreX gene. Prehybridization and hybridization were executed in hybridization tubes with 25 ml of solution at 65° C.

4. Stringency Wash, Exposure, and Development

Stringency washes were performed at differing concentrations of SSC. An initial rinse was performed with 2×SSC, 0.1% SDS at room temperature for 5 minutes. The membranes were then washed in 2×SSC, 0.1% SDS at 65° C. for 30 minutes. The solution was exchanged for 1×SSC, 0.1% SDS and washed for another 30 minutes at 65° C. The membranes were exposed to Kodak BioMax MS film (Eastman Kodak, Rochester, N.Y.) at −80° C. with an amplification screen for approximately 70 hours.

5. Analysis

The genus *Xanthomonas* contains a large number of species and strains that colonize approximately 400 different plant species. Hybridization, or homology, was observed between the hreX gene from *Xanthomonas campestris* pv. *pelargonii*, currently being reported, and the genomes of many of the *Xanthomonas* species tested. A high degree of homology with the hreX gene (determined by the intensity of the hybridization signal) was observed in *Xanthomonas campestris* pv. *campestris, Xanthomonas campestris* pv. *pruni, Xanthomonas campestris* pv. *raphani,* and *Xanthomonas campestris* pv. *vesicatoria.* A weaker homology with the hreX gene was observed in *Xanthomonas oryzae* pv. *oryzicola* and *Xanthomonas oryzae* pv. *oryzae.* These results suggest that a homologue to the hreX gene from *Xanthomonas campestris* pv. *pelargonii* is likely present in species throughout the *Xanthomonas* genus.

Any references which have been incorporated by reference into the specification of this application are intended to be incorporated by reference in their entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated DNA molecule encoding the amino acid sequence of SEQ ID NO:2.

2. The isolated DNA molecule according to claim 1, wherein said DNA molecule comprises the nucleotide sequence of SEQ ID NO: 1.

3. An expression vector comprising the DNA molecule of claim 1 operatively linked to a promoter.

4. The expression vector according to claim 3, wherein the DNA molecule is in sense orientation relative to the promoter.

5. A host cell transformed with the DNA molecule of claim 1.

6. The host cell according to claim 5, wherein the host cell is selected from the group consisting of a plant cell and a bacterial cell.

7. A host cell transformed with the expression vector of claim 4.

8. A transgenic plant transformed with the DNA molecule of claim 1.

9. The transgenic plant according to claim 8, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

10. The transgenic plant according to claim 8, wherein the plant is selected from the group consisting of *Arabidopsis thaliana,* Saintpaulia, petunia, pelargonium, poinsettia, chrysanthemum, carnation, rose, tulip, and zinnia.

11. A transgenic plant seed transformed with the DNA molecule of claim 1.

12. The transgenic plant seed according to claim 11, wherein the plant seed is selected from the group consisting of seeds from alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

13. The transgenic plant seed according to claim 11, wherein the plant seed is selected from the group consisting of seeds from *Arabidopsis thaliana,* Saintpaulia, petunia, pelargonium, poinsettia, chrysanthemum, carnation, rose, tulip, and zinnia 14. A cutting which has been removed from a transgenic plant according to claim 8, which transgenic plant is an ornamental plant, wherein the cutting is characterized by greater resistance to desiccation as compared to a cutting removed from a non-transgenic ornamental plant.

15. A method of imparting disease resistance to a plant, wherein the method comprises transforming a plant with the DNA molecule according to claim 1 to produce a transgenic plant, wherein expression of the DNA molecule imparts disease resistance to the transgenic plant.

16. A method of enhancing growth in a plant, wherein the method comprises transforming a plant with the DNA molecule according to claim 1 to produce a transgenic plant, wherein expression of the DNA molecule enhances growth in the transgenic plant.

17. A method of imparting insect resistance to a plant, wherein the method comprises transforming a plant with the DNA molecule according to claim 1 to produce a transgenic plant, wherein expression of the DNA molecule imparts insect resistance to the transgenic plant.

18. A method of imparting stress resistance to a plant, wherein the method comprises transforming a plant with the DNA molecule according to claim 1 to produce a transgenic plant, wherein expression of the DNA molecule imparts stress resistance to the transgenic plant.

19. A method of imparting resistance to post-harvest disease or desiccation in a fruit or vegetable, wherein the method comprises growing the plant of claim 8 or the seed of claim 15 to produce a grown plant, and harvesting a fruit or vegetable from the grown plant, wherein expression of the DNA molecule imparts disease or desiccation resistance to the fruit or vegetable.

20. A method of reducing desiccation of a cutting of an ornamental plant, wherein the method comprises transforming an ornamental plant with the DNA molecule according to claim 1 to produce a transgenic plant, and removing a cutting from the plant, wherein expression of the DNA molecule imparts desiccation resistance to the cutting.

21. A method of imparting early flowering to a plant, wherein the method comprises transforming a plant with the DNA molecule according to claim 1 to produce a transgenic plant, wherein expression of the DNA molecule imparts early flowering to the transgenic plant.

* * * * *

SEQUENCE LISTING

<160> NUMBER OF SEQ ID NOS: 6

<210> SEQ ID NO 1
<211> LENGTH: 342
<212> TYPE: DNA
<213> ORGANISM: Xanthomonas campestris

<400> SEQUENCE: 1

```
atggactcta tcggaaacaa cttttcgaat atcggcaacc tgcagacgat gggcatcggg      60
cctcagcaac acgaggactc cagccagcag tcgccttcgg ctggctccga gcagcagctg     120
gatcagttgc tcgccatgtt catcatgatg atgctgcaac agagccaggg cagcgatgca     180
aatcaggagt gtggcaacga acaaccgcag aacggtcaac aggaaggcct gagtccgttg     240
acgcagatgc tgatgcagat cgtgatgcag ctgatgcaga accagggcgg cgccggcatg     300
ggcggtggcg gttcggtcaa cagcagcctg ggcggcaacg cc                       342
```

<210> SEQ ID NO 2
<211> LENGTH: 114
<212> TYPE: PRT
<213> ORGANISM: Xanthomonas campestris

<400> SEQUENCE: 2

```
Met Asp Ser Ile Gly Asn Asn Phe Ser Asn Ile Gly Asn Leu Gln Thr
  1               5                  10                  15

Met Gly Ile Gly Pro Gln Gln His Glu Asp Ser Ser Gln Gln Ser Pro
             20                  25                  30

Ser Ala Gly Ser Glu Gln Gln Leu Asp Gln Leu Leu Ala Met Phe Ile
         35                  40                  45

Met Met Met Leu Gln Gln Ser Gln Gly Ser Asp Ala Asn Gln Glu Cys
     50                  55                  60

Gly Asn Glu Gln Pro Gln Asn Gly Gln Gln Glu Gly Leu Ser Pro Leu
 65                  70                  75                  80

Thr Gln Met Leu Met Gln Ile Val Met Gln Leu Met Gln Asn Gln Gly
                 85                  90                  95
```

-continued

```
Gly Ala Gly Met Gly Gly Gly Ser Val Asn Ser Ser Leu Gly Gly
            100                 105                 110
Asn Ala

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
gatcttgccg ttgcagcttt                                              20

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 4
tagcatatgg actctatcgg aaacaactttt t                                 31

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 5
aaggatcctc aggcgttgcc gcccaggctg ctg                               33

<210> SEQ ID NO 6
<211> LENGTH: 408
<212> TYPE: DNA
<213> ORGANISM: Artificial Sequence
<220> FEATURE:
<223> OTHER INFORMATION: Description of Artificial Sequence: probe

<400> SEQUENCE: 6
aattcggctt taccatatgt atccagttca accacatgag acgggaatca ccatggactc    60
tatcggaaac aacttttcga atatcggcaa cctgcagacg atgggcatcg ggcctcagca   120
acacgaggac tccagccagc agtcgccttc ggctggctcc gagcagcagc tggatcagtt   180
gctcgccatg ttcatcatga tgatgctgca acagagccag ggcagcgatg caaatcagga   240
gtgtggcaac gaacaaccgc agaacggtca acaggaaggc ctgagtccgt tgacgcagat   300
gctgatgcag atcgtgatgc agctgatgca gaaccagggc ggcgccggca tgggcggtgg   360
cggttcggtc aacagcagcc tgggcggcaa cgccggatcc ttaagccg               408
```